Figure 1:
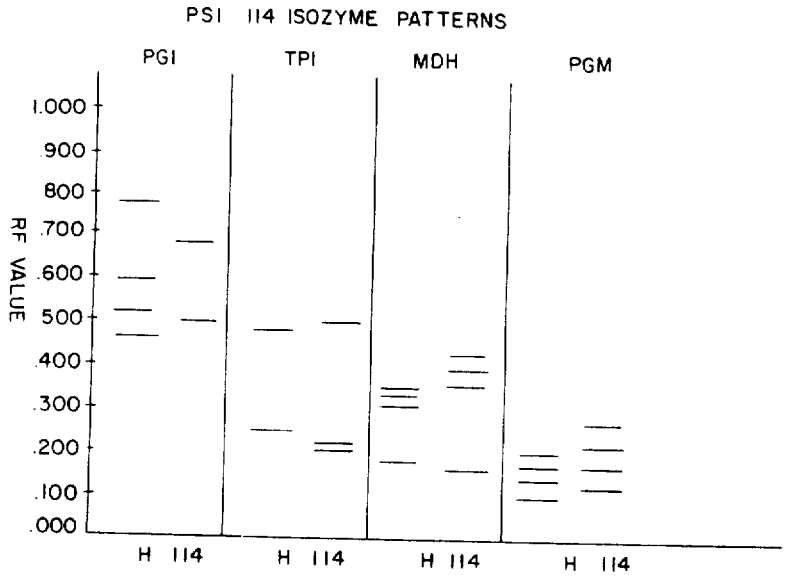

United States Patent [19]

Ackerman

[11] Patent Number: Plant 7,451

[45] Date of Patent: Feb. 19, 1991

[54] RASPBERRY PLANT NAMED PSI 114

[75] Inventor: Stephen M. Ackerman, Salinas, Calif.

[73] Assignee: Plant Sciences, Inc., Watsonville, Calif.

[21] Appl. No.: 398,436

[22] Filed: Aug. 25, 1989

[51] Int. Cl.[5] ..... A01H 5/00

[52] U.S. Cl. ..... Plt./46

[58] Field of Search ..... Plt./46

*Primary Examiner*—Howard J. Locker

*Attorney, Agent, or Firm*—Foley & Lardner, Schwartz, Jeffery, Schwaab, Mack, Blumenthal & Evans

[57] ABSTRACT

This new cultivar of everbearing red raspberry is characterized by high yield (producing 55% of its overall spring production in June), early fruiting habits and exceptional vigor. It fruits 2–3 weeks earlier on second year floricanes than does Willamette.

4 Drawing Sheets

1

My invention relates to a new and distinct cultivar of everbearing red raspberry named PSI 114, botanically known as *Rubus idaeus*. It was discovered by me as a chance seedling in a breeding plot established in 1987 on a ranch in Watsonville, Calif., provided by Well-Pict, Inc., of Watsonville.

This breeding program was initiated jointly by Plant Sciences, Inc. and Coast Cooling, Inc., with the goal of developing new and distinct raspberry varieties. In 1987, this new variety was selected, and extensively tested over the next year.

On Dec. 30, 1987, 15 to 20 dormant sucker canes of the variety were dug from the 1987 seedling field located on the Flats Ranch, Watsonville, Calif. All canes were hand dug as dormant root stock, cleaned, bagged and boxed. The canes were stored at a local cold storage facility at 28° F. until planting. These canes were planted on Jan. 26, 1988, in 15 to 20 linear feet of bed in the 1988 selection field, also located on the Flats ranch.

On Nov. 30, 1988, 100 dormant sucker canes of the variety were dug from the 1988 selection field located on the Flats ranch, for further propagation. The following lists the planting dates, number of plants propagated and location of each planting.

The variety has been reproduced through asexually propagated sucker plants from selection fields in Watsonville, Calif. These daughter plants were then relocated for further testing on local grower fields associated with Well-Pict, Inc., in the Watsonville/Salinas area. Through these further tests and subsequent generations, the characteristics of the novel variety remained fixed and true to type.

| Planting Date | No. Plants | Location/Watsonville, CA |
|---|---|---|
| 12-30-88 | 40* | Peckham Ranch |
| 1-19-89 | 15** | Flats Ranch |
| 1-19-89 | 6* | Nakano Ranch |
| 1-25-89 | 20* | Peckham Ranch |
| 4-30/5-2-89 | 2,000–3,000*** | Flats Ranch |

*Planted as dormant bare root stock for field evaluation.

**Planted as dormant bare root stock for field evaluations in the 1989 advanced selection field.

***Planted for commercial nursery stock as greenhouse matured shoot tips propagated from 8–10 lbs. of roots.

The following features are particularly outstanding in my new variety:

1. Everbearing fruiting habit, fruits on first year primocanes.

2

2. High yield, producing about 55 percent of overall spring production in June.

3. Early fruiting habit in second year floricanes; typically, 2–3 weeks earlier than Willamette, and one week earlier than PSI 168 or PSI 79.

4. Exceptional vigor; producing 3 to 4 times as many suckers as Heritage, and twice as many as PSI 79, PSI 127 or PSI 168.

5. Reduced thorns, about 70 percent smaller than Heritage.

6. Exceptionally small diameter canes.

The accompanying color photographs show typical specimens of this new red raspberry variety at various stages of development.

Photograph 1 shows a section of a typical primocane, with its many small and reduced thorns, foliage, fruit, flowers, and a typical fruiting terminal.

Photograph 2 shows the developmental stages of a berry from flower to maturity, also the purple coloration of a typical primocane.

Photograph 3 shows a typical fruiting terminal, the exposure of the fruit making this variety very easy to pick. The photograph also shows the slight irregular shapes of the drupelets, leading to a slight irregularity of fruit shape.

Photograph 4 shows a typical mature leaf with its deep corrugation.

FIG. 1 illustrates the electrophoresis patterns unique to this variety, as explained in detail below.

Production on first year primocanes begins approximately on July 15, yielding 1.0 percent of its overall production in July, 45 percent in August, 40 percent in September, 10 percent in October, and 4 percent in November, peaking during the last week in August. Berry size averages 2.9–3.1 grams from July through November, (about 10 percent larger than Heritage).

Spring production on second year floricanes begins approximately on May 1, yielding 35 percent of its total production in May, 55 percent in June, and 10 percent in July, peaking during the first week in June. Berry size averages 2.3–2.5 grams from May through July (about 20 percent smaller than Willamette).

The spring crop typically comprises 70 percent of the total production, with the fall crop comprising 30 percent. The spring crop precedes Willamette by approximately 2 weeks, with yields throughout the year exceeding those of both Heritage and Willamette.

The following is a detailed description of my new variety, based upon observations taken in Watsonville, Calif. The color terminology is in accordance with the Munsell Book of Colors, Munsell Color, Baltimore, Md. (1979).

Parentage: An open pollinated seedling of unknown parentage.

Fruit: Conditions when described; late (Oct. 27, 1988).

*Color.*—Red, color 7.5R 3/10 to 7.5R 4/10.

*Size.*—Averages 18.2 mm long×18.9 mm wide (2.5 grams).

*Shape.*—Ovate, tapering to a rounded tip.

*Cavity.*—Funnel shaped, size averages 14.5 mm deep×8.0 mm wide.

*Receptacles.*—Cone shaped, size averages 13.0 mm long×9.5 mm wide at the base, tapering to a sharp point. Color 10Y 9/4 to 10Y 8.5/4.

*Drupelets.*—Small, irregular in shape, averages 70–85 per berry, and 15–16 around the outer rim.

*Seeds.*—Small, averages 2.6 mm long×1.4 mm wide×1.0 mm thick. Average weight, 1.3 milligrams per seed. The surface is rugose. Color tan, 10YR 8/4 to 10YR 7/4.

*Sepals.*—Acuminate, number — 5, color 5GY 6/6 to 5GY 7/6.

*Petals.*—Obovate, number — 5.

*Quality.*—Very good fresh. Holds uniformity in color and appearance through cold storage and shipping. Fruit is well exposed and easy to pick. Detaches easily from receptacle.

Plant: Data are an average of two evaluations, made on Sept. 23, 1988 and Oct. 12, 1988, respectively.

*Growth.*—Vigorous.

*Crown.*—Branched.

*Leaves.*—All samples were taken from a fully mature trifoliate, 10 to 12 trifoliates from the terminal bud. Leaves are moderately corrugated and slightly downwardly cupped. Foliage is nearly always three foliate. Occasionally, the central leaflet will develop points to true independent leaflets, thus, creating a four foliate. Central leaflet: Size — averages 10.6 cm long×9.7 cm wide; Shape — cordate, tapering to an acuminate point; Color — upper surface, 7.5GY 4/4 to 7.5GY 3/4, lower surface, 5GY 7/2 to 5GY 6/2. Lateral leaflet: Size — averages 8.9 cm long×6.7 cm wide; Shape — ovate, tapering to an acuminate point. Petiole: Averages 3.9 to 4.1 cm long and 2.7 to 2.9 mm in diameter.

*Canes.*—Moderately tall, averages from 1.3 to 1.5 meters tall, with an average basal diameter of 1.5 to 1.6 cm. Color, evaluated on Feb. 10, 1989, is light — medium brown, 7.5 YR 4/4 to 7.5 YR 6.4. Internode length averages 4.4 to 4.6 cm at mid cane. Produces on the upper 35 percent of its cane an average of 10 to 11 fruiting laterals, with an average length of up to 47 to 50 cm. Fruit is borne in raceme clusters averaging 6 to 7 berries per terminal prior to the first trifoliate.

*Suckers.*—Produces an average of 13 to 15 suckers per linear foot of bed planted in a single row and spaced 12 inches apart. Average basal diameter — 0.4 to 0.5 cm. Glabrous, with many small soft prickles, heavy at the base, averaging 20 per cm of cane by 1.8 mm long to 7 per cm at the tip by 0.8 mm long. Internode length averages 5.0 to 5.2 cm at mid cane. Color is light green, 5GY 8/2 to 5GY 8/4. With age and exposure to the sun, suckers tend toward a purple coloration, color 10RP 3/8 to 10RP 5/8.

Studies of protein polymorphism in Rubus were carried out to characterize this newly developed variety and distinguish it from other varieties.

Isozymes were extracted from young leaves and characterized using starch gel electrophoresis techniques. The following isozymes were characterized: malate dehydrogenase (MDH: EC 1.1.1.37); triose phosphate isomerase (TPI: EC 5.3.1.1); phosphoglucoisomerase (PGI: EC 5.3.1.9) and phosphoglucomutase (PGM: EC 2.7.5.1).

The plant material used was both field and greenhouse grown in Watsonville, Calif. Newly matured leaves (1 g fresh weight) from the growing tips of canes were used. Samples were held at 4°–8° C. and analyzed within 24 hours of collection.

The tris extraction buffer (pH 8.0) was as follows: 0.05M tris base, 0.007M citric acid (monohydrate), 0.1% cysteine hydrochloride, 0.1% ascorbic acid (Na salt or free acid), 1.0% polyethylene glycol, and 80 ul/l 2-mercaptoethanol. Samples were extracted in 10–12 ml cold buffer by homogenizing at 17,000 rpm.

Gel and electrode buffers for the four enzyme systems analyzed are given in Table 1. Electrophoresis specifications for such enzyme systems are given in Table 2.

The starch gel is prepared as follows, and held overnight at 20±5 C prior to use. Potato starch (30 g) is dissolved in 80 ml of cold gel buffer (System A: gel buffer 50 ml/electrode buffer 30 ml) in a vacuum flask 1 l). Boiling gel buffer (220 ml) is added to the starch solution. Starch is completely dissolved by vigorously swirling the solution in the vacuum flask, and then vacuumed for 15 to 30 seconds. Gel solution is immediately poured onto a 20.5×22.0 cm plexiglass gel plate and covered until use.

Samples are inoculated onto paper wicks and placed in a cooled gel (4 C); then covered with Saran and electrophoresed for 20 minutes. The wicks are removed and the system is run until the dye front travels approximately 5–8 cm.

Following electrophoresis, the gel is sliced into four equal slices and stained for each enzyme system. Banding patterns are interpreted as they develop, and gel slices are fixed in 50% glycerol.

TABLE 1

| SYSTEM | pH | GEL BUFFER | G/L | ELECTRODE BUFFER | G/L | pH |
|---|---|---|---|---|---|---|
| A | 8.3 | Tris Base | 65 | Lithium Hydroxide | 1.2 | 8.3 |
| | | Citric Acid (Monoh) | 1.5 | Boric Acid | 12.0 | |
| B | 7.0 | DL-Histitine HCL (Monohydrate) | 1.2 | Tris Base | 16.5 | 7.0 |
| | | | | Citric Acid (Monohyd) | 9.0 | |
| C | 7.8 | Tris Ultra Pure | 1.09 | Tris Ultra Pure | 16.35 | 7.8 |
| | | Citric Acid | 0.63 | Citric Acid | 9.03 | |
| | | $Na_2EDTA$ | 0.45 | $Na_2EDTA$ | 0.45 | |

TABLE 2

RUBUS ELECTROPHORESIS SPECIFICATIONS

| SYSTEM | ENZYME | pH | CURRENT | GEL SLICE # |
|---|---|---|---|---|
| A | PGI | 8.3 | 275V | 2 |
| A | LAP | 8.3 | 275V | 4 |
| B | MDH | 7.0 | 150V | 2 |

TABLE 2-continued

| RUBUS ELECTROPHORESIS SPECIFICATIONS | | | | |
|---|---|---|---|---|
| SYSTEM | ENZYME | pH | CURRENT | GEL SLICE # |
| B | PGM | 7.0 | 150V | 3 |
| C | TPI | 7.8 | 50mA | 2 |

The isozyme banding patterns for the four enzyme systems compared to those of Heritage are given in FIG. 1. The RF value is the ratio between the distance traveled by the band to the distance (cm) traveled by the dye front (cm).

My new variety may not be resistant to any known diseases and insects. It is known to be susceptible to powdery mildew and rust. This new variety may vary slightly in its characteristics, depending upon weather, soil, location, and evaluation dates.

What is claimed is:

1. A new distinct variety of red raspberry plant named PSI 114, as herein described and illustrated.

* * * * *

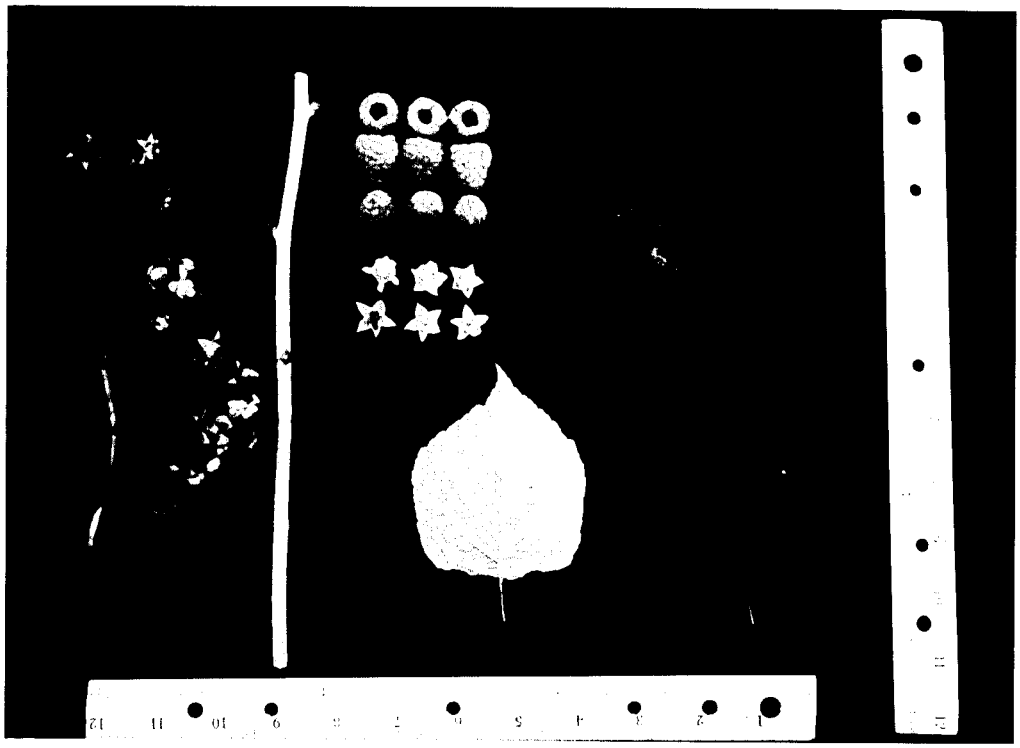

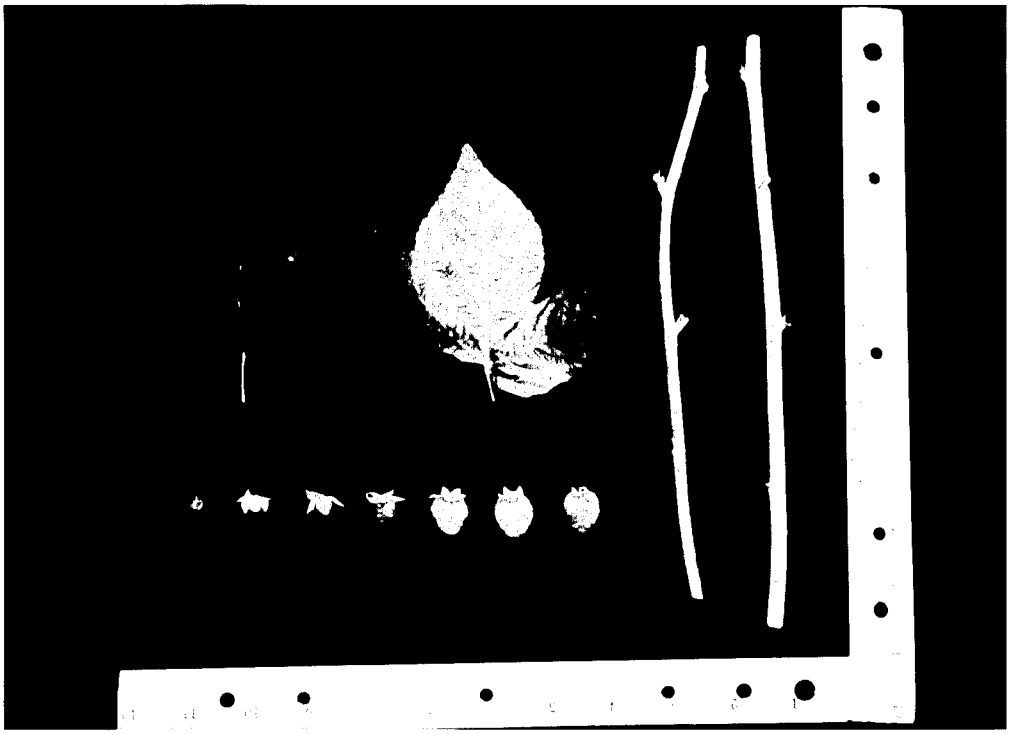

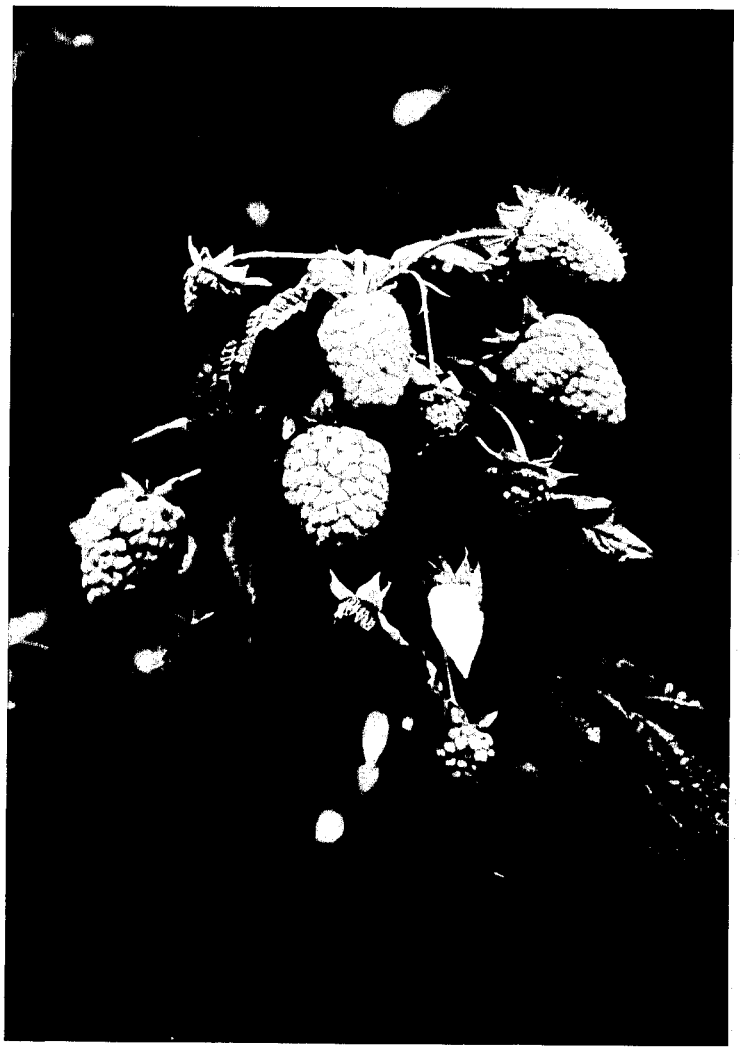

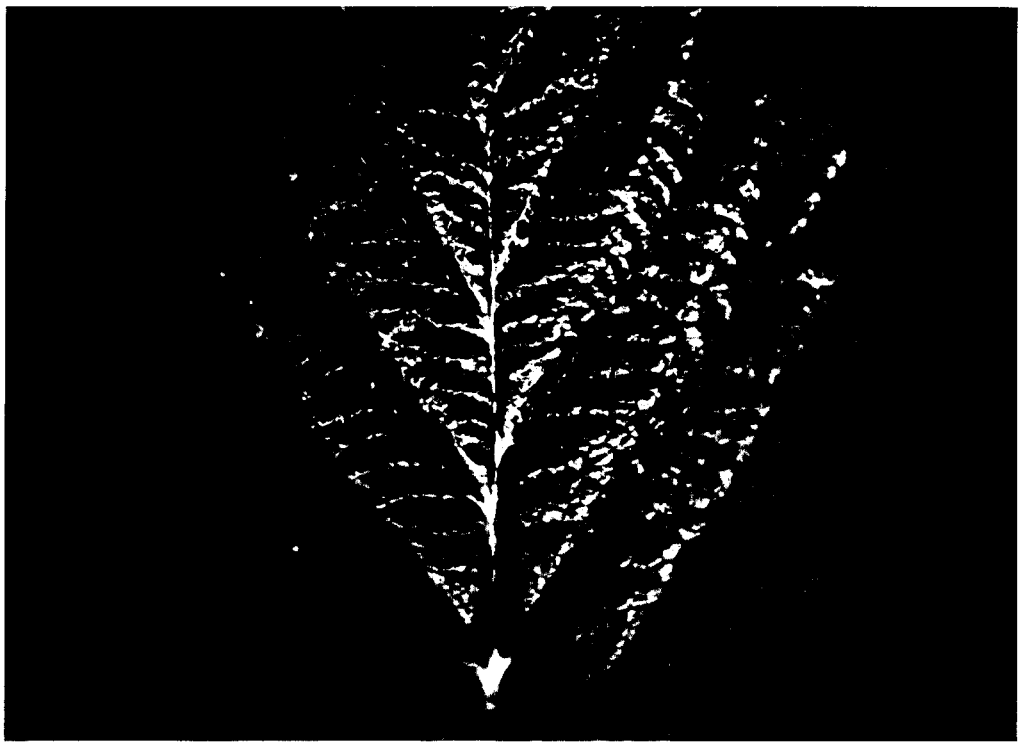

UNITED STATES PATENT AND TRADEMARK OFFICE

CERTIFICATE OF CORRECTION

PATENT NO. : PP7,451

DATED : February 19, 1991

INVENTOR(S) : Stephen Ackerman

It is certified that error appears in the above-identified patent and that said Letters Patent is hereby corrected as shown below:

Column 2 of the heading, line 10, delete "4" and insert --5--.

Add attached Figure 1 to the drawing sheets and identify Figure 1 by the heading --Sheet 5 of 5--.

Reidentify Sheet 1 as --Sheet 1 of 5--.

Reidentify Sheet 2 as --Sheet 2 of 5--.

Reidentify Sheet 3 as --Sheet 3 of 5--.

Reidentify Sheet 4 as --Sheet 4 of 5--.

Column 4, lines 32 and 33, delete "1ℓ)" and insert --(1.0ℓ)--.

Signed and Sealed this

Seventh Day of April, 1992

*Attest:*

*Attesting Officer*

HARRY F. MANBECK, JR.

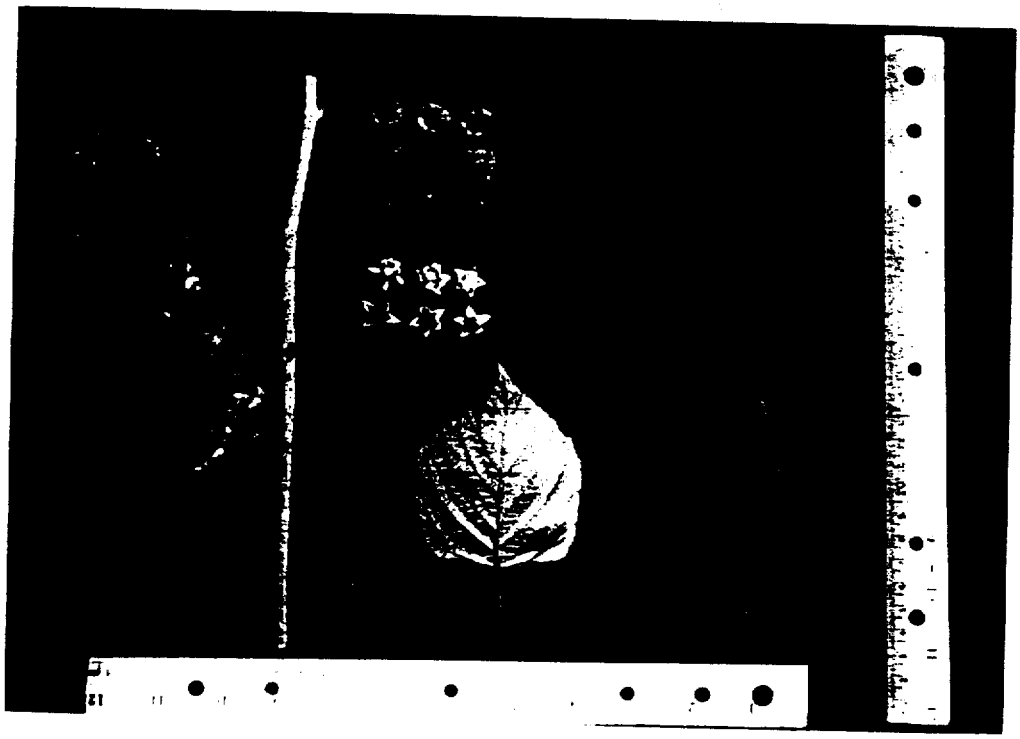

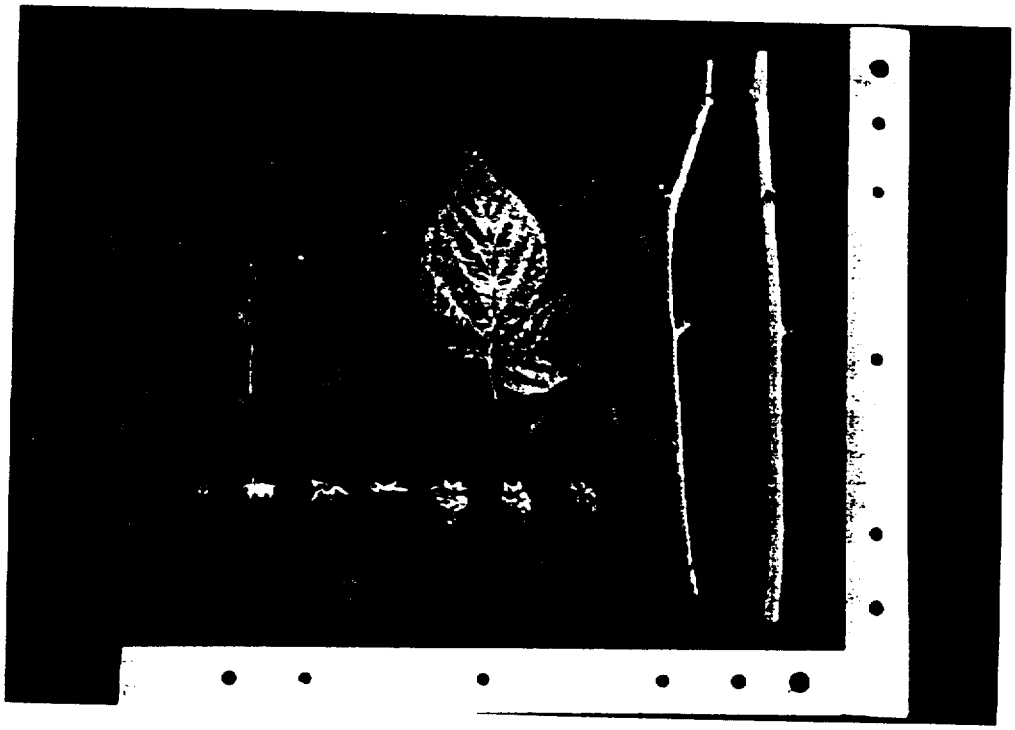

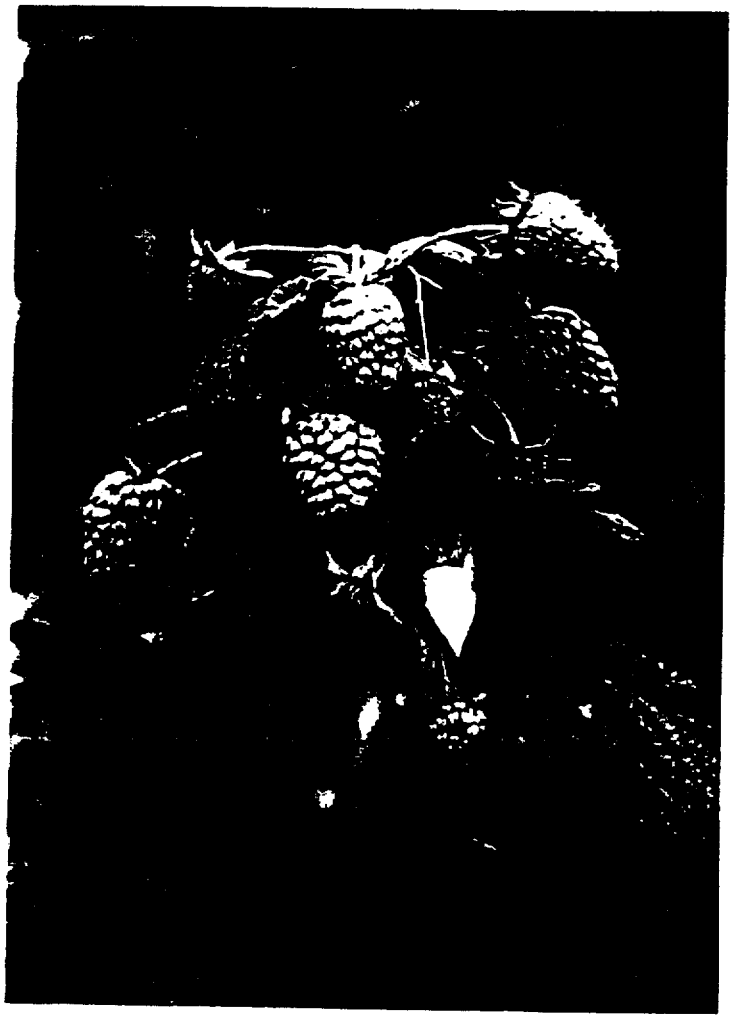

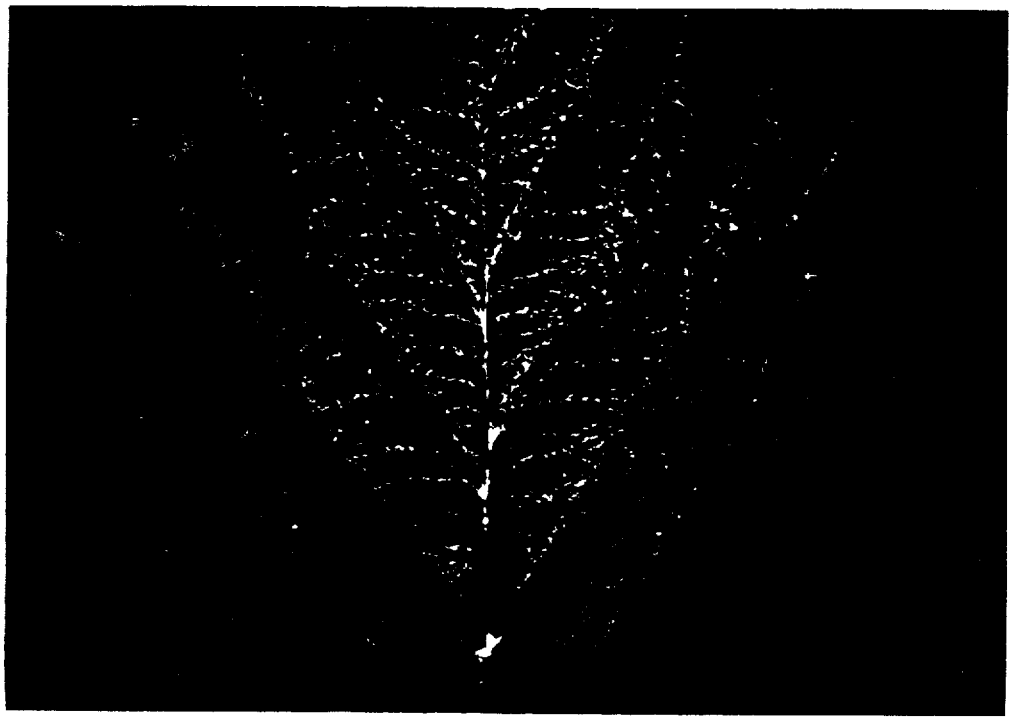

*Commissioner of Patents and Trademarks*